US010657671B2

(12) United States Patent
Avendi et al.

(10) Patent No.: US 10,657,671 B2
(45) Date of Patent: May 19, 2020

(54) SYSTEM AND METHOD FOR NAVIGATION TO A TARGET ANATOMICAL OBJECT IN MEDICAL IMAGING-BASED PROCEDURES

(71) Applicant: Avent, Inc., Alpharetta, GA (US)

(72) Inventors: Michael R. Avendi, Irvine, CA (US); Shane A. Duffy, Irvine, CA (US); Kenneth C. Hsu, Tustin, CA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 15/736,129

(22) PCT Filed: Jun. 29, 2017

(86) PCT No.: PCT/US2017/039928
§ 371 (c)(1),
(2) Date: Dec. 13, 2017

(87) PCT Pub. No.: WO2018/101985
PCT Pub. Date: Jun. 7, 2018

(65) Prior Publication Data
US 2019/0355149 A1 Nov. 21, 2019

Related U.S. Application Data

(60) Provisional application No. 62/429,150, filed on Dec. 2, 2016.

(51) Int. Cl.
*G06T 7/73* (2017.01)
*A61B 34/20* (2016.01)
*G16H 30/40* (2018.01)

(52) U.S. Cl.
CPC ............... *G06T 7/74* (2017.01); *A61B 34/20* (2016.02); *A61B 2034/2063* (2016.02);
(Continued)

(58) Field of Classification Search
CPC ............. G06T 7/74; G06T 2207/30004; G06T 2207/20084; G06T 2207/10132; A61B 34/20; A61B 2034/2063; G16H 30/40
See application file for complete search history.

(56) References Cited

U.S. PATENT DOCUMENTS 7,876,934 B2 1/2011 Georgescu et al.
8,073,220 B2 12/2011 Khamene et al.
(Continued)

FOREIGN PATENT DOCUMENTS

JP 2005199403 A 7/2005
JP 2008017997 A 1/2008
(Continued)

OTHER PUBLICATIONS

Hadjerci et al., "On-line Learning Dynamic Models for Nerve Detection in Ultrasound Videos", 2016 IEEE International Conference on Image Processing, Sep. 25, 2016, pp. 131-135.
(Continued)

*Primary Examiner* — Yon J Couso
(74) *Attorney, Agent, or Firm* — Dority & Manning, P.A.

(57) ABSTRACT

The present invention is directed to a system and method for providing navigational directions to a user to locate a target anatomical object during a medical procedure via a medical imaging system. The method includes selecting an anatomical region surrounding the object; generating a plurality of real-time two-dimensional images of scenes from the anatomical region and providing the plurality of images to a controller; developing and training a deep learning network to automatically detect and identify the scenes from the anatomical region; automatically mapping each of the plurality of images from the anatomical region based on a relative spatial location and a relative temporal location of each of the identified scenes in the anatomical region via the deep learning network; and providing directions to the user
(Continued)

to locate the object during the medical procedure based on the relative spatial and temporal locations of each of the identified scenes.

25 Claims, 11 Drawing Sheets

(52) U.S. Cl.
CPC ............... *G06T 2207/10132* (2013.01); *G06T 2207/20084* (2013.01); *G06T 2207/30004* (2013.01); *G16H 30/40* (2018.01)

(56) References Cited

U.S. PATENT DOCUMENTS

| | | | |
|---|---|---|---|
| 8,867,802 B2 | 10/2014 | Criminisi et al. | |
| 9,153,022 B2 | 10/2015 | Finkelstein et al. | |
| 9,256,962 B2 | 2/2016 | Berry et al. | |
| 9,384,413 B2 | 7/2016 | John et al. | |
| 2003/0133611 A1 | 7/2003 | Deco et al. | |
| 2003/0174881 A1 | 9/2003 | Simard et al. | |
| 2010/0010348 A1 | 1/2010 | Halmann | |
| 2011/0182493 A1 | 7/2011 | Huber et al. | |
| 2011/0188715 A1 | 8/2011 | Shotton et al. | |
| 2013/0336553 A1 | 12/2013 | Buisseret et al. | |
| 2014/0129200 A1 | 5/2014 | Bronstein et al. | |
| 2014/0314290 A1 | 10/2014 | Dabbah et al. | |
| 2015/0148657 A1 | 5/2015 | Shashar et al. | |
| 2015/0164605 A1 | 6/2015 | Patwardhan et al. | |
| 2015/0173701 A1 | 6/2015 | Major et al. | |
| 2015/0265251 A1 | 9/2015 | Cho | |
| 2016/0012604 A1 | 1/2016 | Firouzian et al. | |
| 2016/0042510 A1 | 2/2016 | Littell | |
| 2016/0042511 A1 | 2/2016 | Chukka et al. | |
| 2016/0058422 A1 | 3/2016 | Lee et al. | |
| 2016/0092748 A1 | 3/2016 | Koktava et al. | |
| 2016/0106321 A1 | 4/2016 | Sharma et al. | |
| 2016/0125595 A1 | 5/2016 | Silbert et al. | |
| 2016/0174902 A1 | 6/2016 | Georgescu et al. | |
| 2016/0287214 A1 | 10/2016 | Ralovich et al. | |
| 2016/0328643 A1 | 11/2016 | Liu et al. | |
| 2017/0265943 A1* | 9/2017 | Sela | G06F 19/00 |
| 2017/0265947 A1* | 9/2017 | Dyer | A61B 34/20 |

FOREIGN PATENT DOCUMENTS

| | | |
|---|---|---|
| WO | WO 2013/179188 A1 | 12/2013 |
| WO | WO 2015/092582 AI | 6/2015 |
| WO | WO 2015/104607 A1 | 7/2015 |
| WO | WO 2015/109254 A2 | 7/2015 |
| WO | WO 2015/175806 A1 | 11/2015 |
| WO | WO 2015/191414 A2 | 12/2015 |

OTHER PUBLICATIONS

Reddy D. Manikanta, "On segmentation of Nerve Structures in Ultrasound Images", retrieved from the Internet: https://manikantareddvd.github.io/posts/2016/11/16/ultrasound-nerve-segmentations, Nov. 16, 2016, pp. 1-27.

International Search Report for PCT/US2017/039928, dated Oct. 10, 2017, 13 pages.

* cited by examiner

SYSTEM AND METHOD FOR NAVIGATION TO A TARGET ANATOMICAL OBJECT IN MEDICAL IMAGING-BASED PROCEDURES

CROSS REFERENCE TO RELATED APPLICATIONS

The present application is the national stage entry of International Patent Application No. PCT/US2017/039928 having a filing date of Jun. 29, 2017, which claims priority to U.S. Provisional Application Ser. No. 62/429,150, having a filing date of Dec. 2, 2016, the entire contents of which are incorporated by reference.

FIELD OF THE INVENTION

The present invention relates to detection and identification of anatomical objects in the field of medical imaging, and more particularly, to a system and method for providing navigational directions to reach a target anatomical object in medical imaging-based procedures such as ultrasound-guided regional anesthesia based on the detection and identification of anatomical objects contained within a plurality of images taken of scenes from around the target anatomy.

BACKGROUND

Various imaging systems based on traditional approaches exist for assisting the medical professional in identifying the gross region of a target anatomical object, such as ultrasound, computed tomography (CT), magnetic resonance (MR), and fluoroscopic imaging systems. However, anatomical object detection using such systems is not always robust, especially for some challenging detection problems in which the anatomical objects exhibit large variations in anatomy, shape, and/or appearance, as well as noise and artifacts in the medical images. As a result, it is often difficult for a medical professional to quickly and accurately locate the gross region of the target anatomical object when using such imaging systems. For instance, nerve blocks or peripheral nerve blocks (PNBs) are a type of regional anesthesia used for surgical anesthesia as well as for both postoperative and nonsurgical analgesia where it is desired to accurately locate a target anatomical object (e.g., a target nerve). During a PNB, a medical professional injects an anesthetic near a target nerve or bundle of nerves to block sensations of pain from a specific area of the body. However, it can be challenging for a medical professional to quickly and accurately locate the gross region of the target nerve when using currently available imaging systems. For example, for certain nerve block procedures, it is often difficult for a physician to quickly and accurately locate a target nerve bundle via an ultrasound imaging system.

Accordingly, the present disclosure is directed to a system and method for automatic detection, identification, and mapping of anatomical objects from a plurality of real-time images of scenes taken from an anatomical region surrounding a target anatomical object (e.g., a target nerve) in order to provide directions to a user (e.g., medical professional), thus enabling the user to quickly and accurately reach the target anatomical object of interest using deep learning networks that can be implemented via existing imaging systems.

SUMMARY OF THE INVENTION

Objects and advantages of the invention will be set forth in part in the following description, or may be obvious from the description, or may be learned through practice of the invention.

In one aspect, the present invention is directed to a method for providing navigational directions to a user to locate a target anatomical object during a medical procedure via a medical imaging system. The method includes selecting an anatomical region surrounding the target anatomical object; generating a plurality of real-time two-dimensional images of scenes from the anatomical region surrounding the target anatomical object and providing the plurality of real-time two-dimensional images to a controller; developing and training a deep learning network to automatically detect and identify the scenes from the anatomical region surrounding the target anatomical object; automatically mapping each of the plurality of real-time two-dimensional images from the anatomical region surrounding the target anatomical object based on a relative spatial location and a relative temporal location of each of the identified scenes in the anatomical region via the deep learning network; and providing directions to the user to locate the target anatomical object during the medical procedure based on the relative spatial location and the relative temporal location of each of the identified scenes.

In one particular embodiment, the medical procedure can be a nerve block, wherein the target anatomical object is a target nerve. Further, the nerve block can be an interscalene nerve block, a supraclavicular nerve block, an infraclavicular nerve block, an axillary nerve block, a femoral nerve block, a sciatic nerve block, an adductor canal nerve block, a popliteal nerve block, a saphenous nerve block, a fascia iliaca nerve block, a thoraco lumbar paravertebral nerve block, a transversus abdominus plane (TAP) nerve block, an intercostal nerve block, or a thoracic paravertebral nerve block.

In another embodiment, the deep learning network can include at least one of one or more convolutional neural networks or one or more recurrent neural networks.

In still another embodiment, the method can further include developing and training the deep learning network to automatically detect and identify the scenes from the anatomical region surrounding the target anatomical object via ground truth data. Further, developing and training the deep learning network to automatically detect and identify the scenes from the anatomical region surrounding the target anatomical object can include scanning and collecting a dataset of a plurality of images of the scenes from the anatomical region surrounding the target anatomical object from each of a plurality of patients, annotating the dataset of images based on user input to create the ground truth data; dividing the dataset of images and the ground truth data into a training dataset and a validation dataset; and utilizing the training dataset to train the deep learning network.

In yet another embodiment, utilizing the training dataset to train the deep learning network further can include optimizing a cost function to minimize an error between an output of the deep learning network and the ground truth data. Further, optimizing the cost function to minimize the error further can include utilizing a stochastic gradient descent (SGD) algorithm that iteratively processes portions of the ground truth data and adjusts one or more parameters of the deep learning network based on the error between the output of the deep learning network and the ground truth data.

In one more embodiment, after optimizing the cost function, the method can include utilizing the deep learning network in real-time to automatically provide predictions on the validation data and comparing the predictions with the ground truth data.

In an additional embodiment, annotating the dataset of images based on user input to create the ground truth data can further include manually identifying and annotating the target anatomical object, additional anatomical objects, landmarks, tissue, or a combination thereof in each image of the dataset.

In another embodiment, the method can include initially training the deep learning network to automatically detect and identify the scenes from the anatomical region surrounding the target anatomical object offline.

In still another embodiment, the method can include continuously training the deep learning network to automatically detect and identify the scenes from the anatomical region surrounding the target anatomical object online.

In yet another embodiment, the directions can be provided to the user in annotated form via a user display of the imaging system as a probe scans the anatomical region of interest, wherein the imaging system simultaneously generates the plurality of real-time two-dimensional images.

In one more embodiment, directions can be provided to the user in audio form as a probe scans the anatomical region of interest, wherein the imaging system simultaneously generates the plurality of real-time two-dimensional images.

In an additional embodiment, the medical imaging system can include an ultrasound imaging system, a computed tomography (CT) imaging system, a magnetic resonance (MR) imaging system, or a fluoroscopic imaging system.

In another aspect, the present invention is directed to a medical imaging system for use in a medical procedure. The medical imaging system includes at least one controller configured to perform one or more operations and a user display configured to display the plurality of real-time two-dimensional images to a user. The one or more operations includes receiving a plurality of real-time two-dimensional images of scenes from an anatomical region surrounding a target anatomical object; developing and training a deep learning network to automatically detect and identify the scenes from the anatomical region surrounding the target anatomical object; automatically mapping each of the plurality of real-time two-dimensional images from the anatomical region surrounding the target anatomical object based on a relative spatial location and a relative temporal location of each of the identified scenes in the anatomical region via the deep learning network; and providing directions to the user to locate the target anatomical object during the medical procedure based on the relative spatial location and the relative temporal location of each of the identified scenes.

In one particular embodiment, the medical procedure can be a nerve block, wherein the target anatomical object is a target nerve.

In another embodiment, the deep learning network can include at least one of one or more convolutional neural networks or one or more recurrent neural networks.

In still another embodiment, the operation of developing and training the deep learning network to automatically detect and identify scenes from the anatomical region surrounding the target anatomical object can be accomplished via ground truth data. For instance, developing and training the deep learning network to automatically detect and identify scenes from the anatomical region surrounding the target anatomical object can include scanning and collecting a dataset of a plurality of images of scenes from the anatomical region surrounding the target anatomical object from each of a plurality of patients; annotating the dataset of images based on user input to create the ground truth data; dividing the dataset of images and the ground truth data into a training dataset and a validation dataset; and utilizing the training dataset to train the deep learning network.

Further, annotating the dataset of images based on user input to create the ground truth data can include manually identifying and annotating the target anatomical object, additional anatomical objects, landmarks, tissue, or a combination thereof in each image of the dataset.

In yet another embodiment, the controller can be configured to initially train the deep learning network to automatically detect and identify scenes from the anatomical region surrounding the target anatomical object offline.

In an additional embodiment, the controller can be configured to continuously train the deep learning network to automatically detect and identify scenes from the anatomical region surrounding the target anatomical object online.

In still another embodiment, the controller can provide directions to the user in annotated form via the user display as a probe scans the anatomical region of interest, wherein the imaging system simultaneously generates the plurality of real-time two-dimensional images.

In one more embodiment, the controller can provide directions to the user in audio form as a probe scans the anatomical region of interest, wherein the imaging system simultaneously generates the plurality of real-time two-dimensional images.

In another embodiment, the medical imaging system can include an ultrasound imaging system, a computed tomography (CT) imaging system, a magnetic resonance (MR) imaging system, or a fluoroscopic imaging system.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

In another embodiment, the medical imaging system can be configured as a software package to be installed and hosted by other medical imaging systems, wherein the medical imaging system can receive images from a host medical imaging system and provide outputs to be deployed by the host medical imaging system.

In another embodiment, the deep learning network can employ quantized weights, binary weights, and other compression methods to reduce memory usage and accelerate the execution time, such as when limited computation power is available.

In another embodiment, the medical imaging system can employ various transformation, equalization, and normalization techniques to be able to work with different medical imaging systems having different settings, specifications, and image quality.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
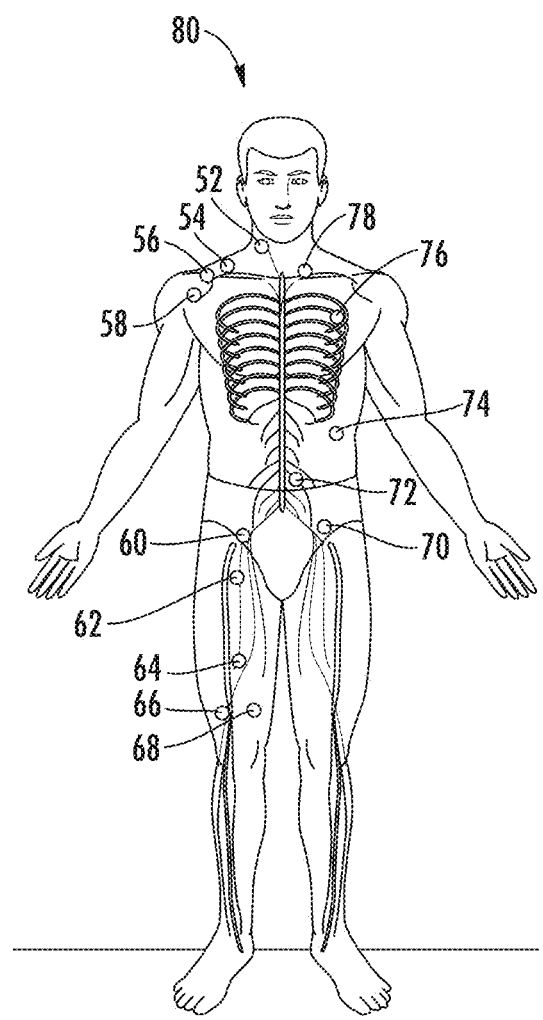
FIG. 1 illustrates the location of various nerve blocks where the method and system of the present disclosure can be utilized to navigate medical professionals to a precise location in conjunction with ultrasound guidance.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Generally, the present disclosure is directed to a system and method for providing navigational directions to a user (e.g., medical professional) to locate a target anatomical object during a medical procedure via a medical imaging system. The method includes selecting an anatomical region surrounding the object; generating a plurality of real-time two-dimensional images of scenes from the anatomical region and providing the plurality of images to a controller; developing and training a deep learning network to automatically detect and identify the scenes from the anatomical region; automatically mapping each of the plurality of images from the anatomical region based on a relative spatial location and a relative temporal location of each of the identified scenes in the anatomical region via the deep learning network; and providing directions to the user to locate the object or to reach the object with a surgical instrument (e.g., needle guide assembly, catheter, needle, scalpel, knife, probe, etc.) during the medical procedure based on the relative spatial and temporal locations of each of the identified scenes.

In one particular embodiment, the present disclosure is directed to an imaging system and method for providing navigational directions to a user (e.g., medical professional) to locate or reach a target nerve of interest to deliver a nerve block to a patient using a plurality of real-time two-dimensional images of scenes from an anatomical region surrounding the target nerve generated by the imaging system, such as an ultrasound imaging system. Referring to FIG. 1, the target nerve can be associated with the delivery of a nerve block to a patient 80. Examples of nerve blocks contemplated by the present disclosure include an interscalene nerve block 52, a supraclavicular nerve block 54, an infraclavicular nerve block 56, an axillary nerve block 58, a femoral nerve block 60, a sciatic nerve block 62, an adductor canal nerve block 64, a popliteal nerve block 66, a saphenous nerve block 68, a fascia iliaca nerve block 70, a thoraco lumbar paravertebral nerve block 72, a transversus abdominus plane (TAP) nerve block 74, an intercostal nerve block 76, a thoracic paravertebral nerve block 78, and the like.

Figure 2:
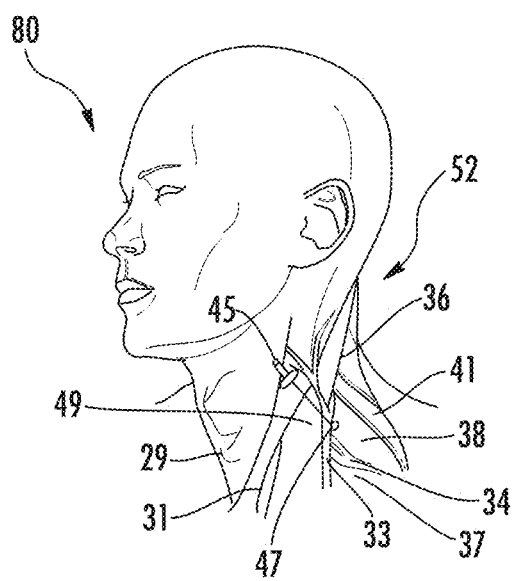
FIG. 2 illustrates the location of the interscalene nerve block of FIG. 1 in more detail.

For example, a detailed view of the anatomical region surrounding an interscalene nerve block 52 is shown in FIG. 2 for reference. Specifically, the anatomical region includes cricoid cartilage 29, the internal jugular vein 31, the external jugular vein 33, the brachial plexus 34, the sternocleidomastoid muscle 36, the anterior scalene muscle 37, the middle scalene muscle 38, and the posterior scalene muscle 41. Using the system and method of the present disclosure, the various anatomical objects or structures discussed above can be detected, identified/labeled, and mapped as discussed in more detail below so that a medical professional can be provided with directions to quickly and accurately insert a needle 45 into the target nerve 49 at needle insertion site 47 to deliver an anesthetic, resulting in an interscalene nerve block 52.

Figure 3:
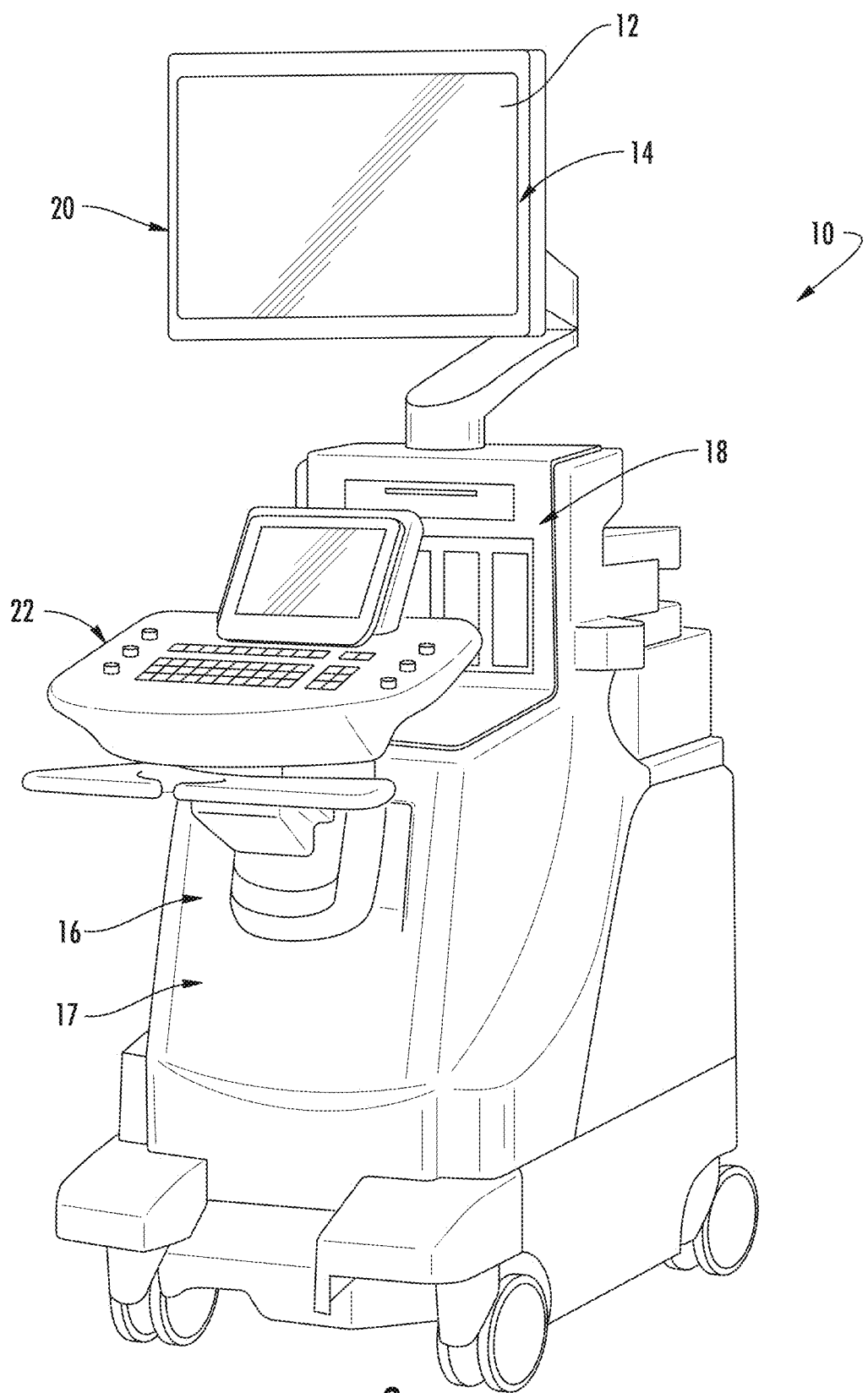
FIG. 3 illustrates a perspective view of one embodiment of an imaging system according to the present disclosure.
Figure 4:
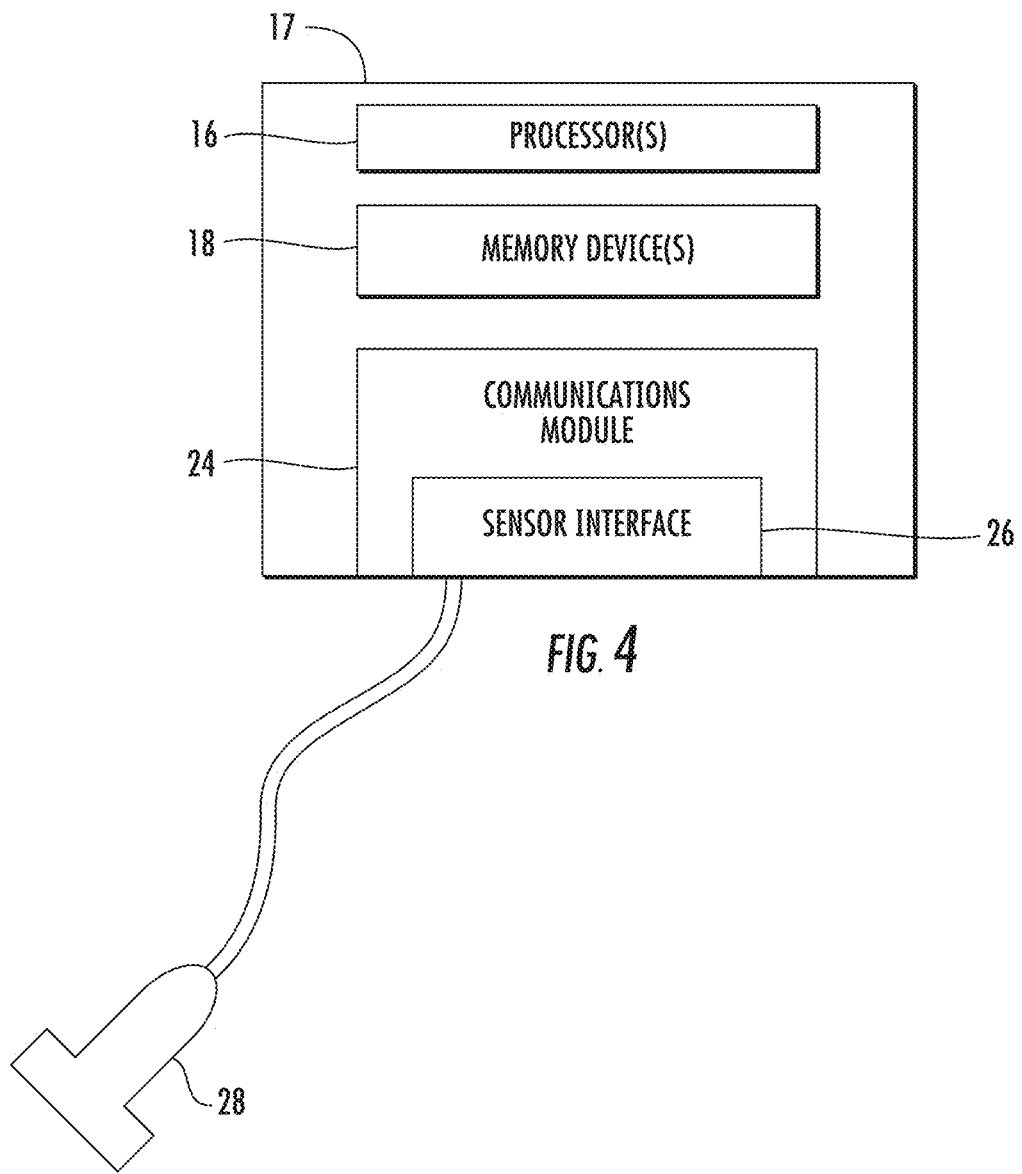
FIG. 4 illustrates a block diagram one of embodiment of a controller of an imaging system according to the present disclosure.

Turning now to FIGS. 3 and 4, one embodiment of an imaging system 10 configured to receive and organize a plurality of individual images 14 generated by the imaging system 10 in real-time is shown. As used herein, the imaging system 10 may correspond to an ultrasound imaging system (as shown), a computer tomography (CT) scanner, a magnetic resonance imaging (MRI) scanner, or any other suitable imaging system that can benefit from the present technology. More specifically, as shown, the imaging system 10 can include a controller 17 configured to receive and organize the plurality of images 14 generated by the imaging system 10. The controller 17 generally includes one or more processor(s) 16 and associated memory device(s) 18 configured to perform a variety of computer-implemented functions (e.g., performing the methods and the like and storing relevant data as disclosed herein), as well as a user display 20. For instance, the processor 16 can be configured to detect, identify, and map a plurality of scenes 12 contained within each image 14 generated by the imaging system 10 from a plurality of real-time two-dimensional ultrasound images 46 is shown. In addition, the imaging system 10 can include a user interface 22, such as a computer and/or keyboard, configured to assist a user in generating and/or manipulating the plurality of scenes 12 contained within each individual image 14.

Additionally, as shown in FIG. 4, the controller 17 may also include a communications module 24 to facilitate communications between the controller 17 and the various components of the imaging system 10, e.g. any of the components of FIGS. 3 and 4. Further, the communications module 24 may include a sensor interface 26 (e.g., one or more analog-to-digital converters) to permit signals transmitted from one or more imaging system probes 28 (e.g., the ultrasound probe) to be converted into signals that can be understood and processed by the controller 17 and/or processor(s) 16. It should be appreciated that the probe 28 may be communicatively coupled to the communications module 24 using any suitable means. For example, as shown in FIG. 4, the probe 28 may be coupled to the sensor interface 26 via a wired connection. However, in other embodiments, the probe 28 may be coupled to the sensor interface 26 via a wireless connection, such as by using any suitable wireless communications protocol known in the art. As such, the controller 17 may be configured to receive one or more signals from the probe 28.

As used herein, the term "controller" refers not only to integrated circuits referred to in the art as being included in a computer, but also refers to a microcontroller, a microcomputer, a programmable logic controller (PLC), an application specific integrated circuit, a field-programmable gate array (FPGA), and other programmable circuits. The controller 17 is also configured to compute advanced control algorithms and communicate to a variety of Ethernet or serial-based protocols (Modbus, OPC, CAN, etc.). Furthermore, in certain embodiments, the controller 17 may communicate with a server through the Internet for cloud computing in order to reduce the computation time and burden on the local device. Additionally, the memory device(s) 18 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 18 may generally be configured to store suitable computer-readable instructions that, when implemented by the controller 17, configure the processor(s) 16 to perform the various functions as described herein.

Figure 5:
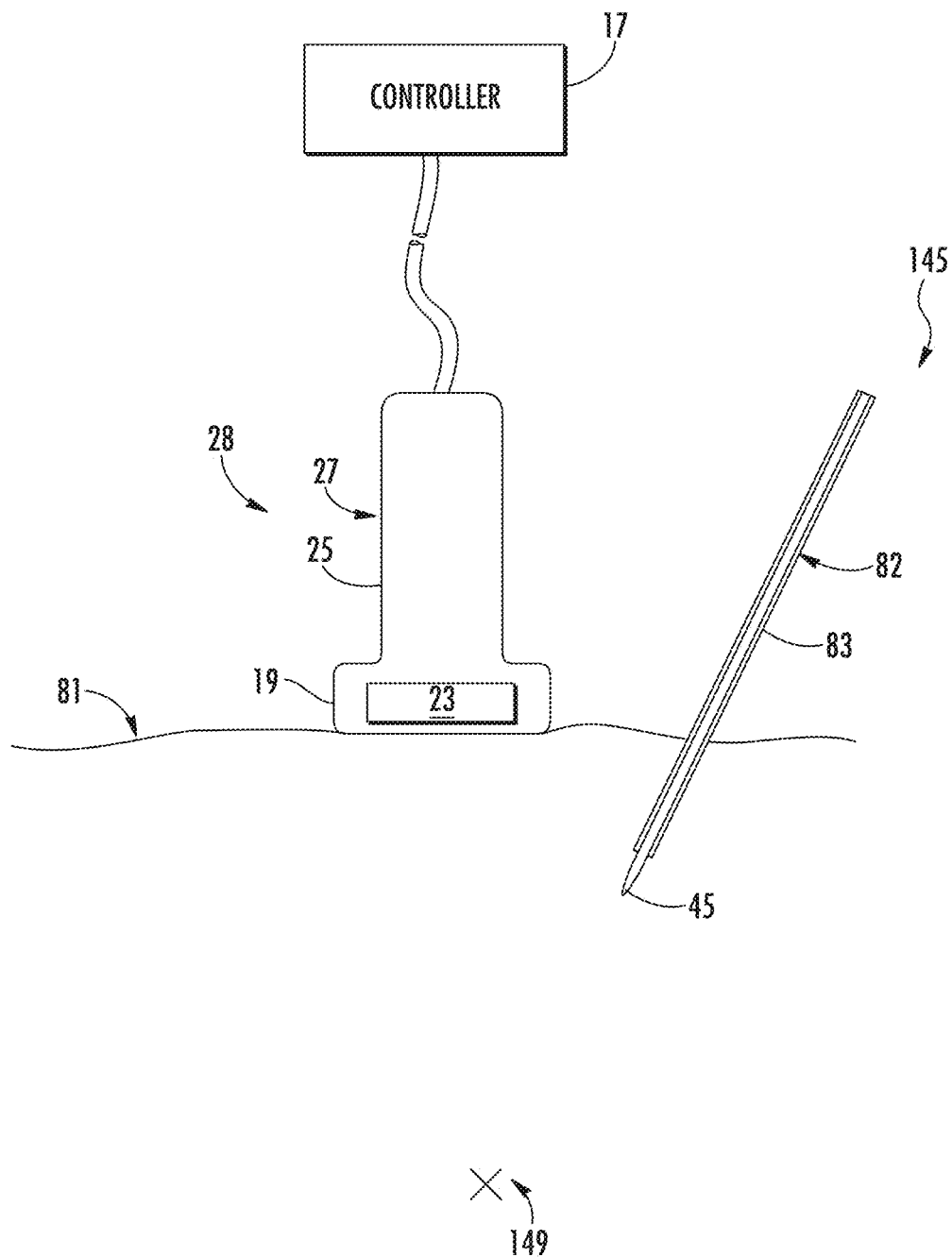
FIG. 5 illustrates a schematic diagram of one embodiment of an ultrasound imaging system according to the present disclosure, particularly illustrating an ultrasound probe used in conjunction with a needle guide to facilitate navigation of a needle towards a target nerve of a patient.
Figure 6:
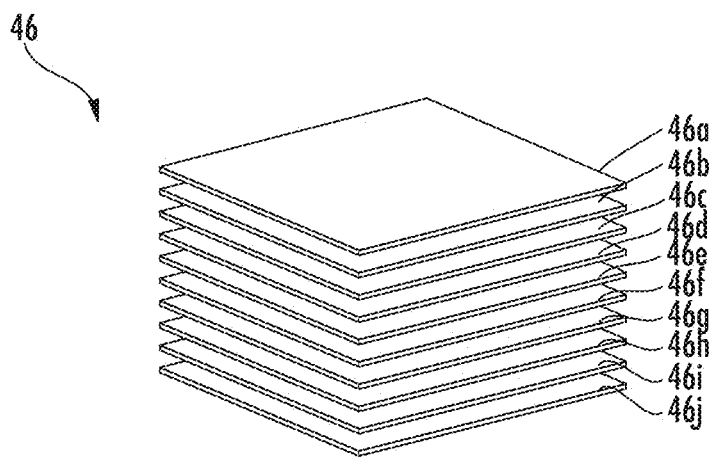
FIG. 6 illustrates a plurality of real-time two-dimensional images collected from an anatomical region surrounding a target anatomical object of interest using the system and method of the present disclosure, where the anatomical object of interest, additional anatomical objects, and landmarks in the scenes contained in the images can be identified and labeled.

Turning now to FIG. 5, when the imaging system 10 is an ultrasound imaging system, the probe 28 (e.g., ultrasound probe) of the imaging system 10 can include a transducer housing 27 and a transducer transmitter 23 mounted therein. As is generally understood, the transducer transmitter 23 is configured to emit and/or receive ultrasound beams. As such, the transducer transmitter 16 may be configured within the internal cavity (not numbered) such that the transducer transmitter 16 is configured to scan an anatomical region surrounding a target anatomical object 149 (e.g., target nerve) of a patient. The imaging system 10 may also include an instrument 145 that is used during any suitable medical procedure, where the instrument 145 is coupled to the probe 28 via the controller 17 in any suitable manner (e.g., wireless, wired, etc.), where the location of the instrument 145 can be determined via the methods described herein. When the medical procedure is a nerve block procedure, the instrument 145 can be a needle guide assembly 82 communicatively coupled to the ultrasound probe 28 via the controller 17, where the controller 17 can be configured to locate the needle guide assembly 82 as it is being moved towards the target anatomical object 149 (e.g., the target nerve) to deliver an anesthetic via a needle 45. It is to be understood, however, that any instrument such as a scalpel, knife, laparoscopic or arthroscopic probe, etc. can be used instead of the needle guide assembly 82 depending on the procedure being performed by the medical professional.

More specifically, as shown, the needle guide assembly 82 may include, at least, a needle 45 and a catheter 83. As such, it should be understood that the needle 45 as well as the catheter 83 of the needle guide assembly 82 can be inserted through the skin 81 the patient 80 in any particular order or simultaneously. For example, in one embodiment, the ultrasound imaging system 10 may include an over-the-needle (OTN) catheter assembly in which the catheter 83 is coaxially mounted over the needle 45. Alternatively, the needle 45 may be mounted over the catheter 83. In such embodiments, the needle 45 may act as an introducer such that it places the catheter 83 at the target nerve 49 and is later removed.

Referring now to FIGS. 6-14, schematic diagrams (FIGS. 6-9) and a flow diagram (FIG. 10) of one embodiment of a method 100 for the automatic detection, identification, and mapping of anatomical objects contained within a plurality of scenes 12 taken from a plurality of real-time two-dimensional images 46 generated by an imaging system 10 to provide directions to a user are illustrated, as are various embodiments of screen shots (FIGS. 11-14) from the user display 20 illustrating an image 14 containing a scene 12 generated from one of the plurality of real-time two-dimensional images 46 when an ultrasound imaging system is used. In certain embodiments, the target anatomical object (s) of interest 30 and the surrounding additional anatomical objects 32 as described herein may include any anatomy structure and/or surrounding tissue of the anatomy structure of a patient. More specifically, as shown in the illustrated embodiments of FIGS. 11-14, when a nerve block procedure is to be completed, and specifically when the nerve block procedure is an interscalene nerve block, the anatomical object of interest 30 that can be detected, identified, and mapped can be an interscalene brachial plexus (BP) 34 of the patient, which generally corresponds to the network of nerves running from the spine, formed by the anterior rami of the lower four cervical nerves and first thoracic nerve. As such, the brachial plexus 34 passes through the cervicoaxillary canal in the neck, over the first rib, and into the axilla (i.e. the armpit region), where it innervates the upper limbs and some neck and shoulder muscles. Further, the surrounding additional anatomical objects 32 (e.g., tissue) of the brachial plexus 34 generally correspond to the sternocleidomastoid muscle (SM) 36, the middle scalene muscle (MCM) 38, the anterior scalene muscle (ASM) 40, and/or similar. The field of view or scene 12 of such anatomical objects 30 and 32 is generally difficult for physicians to navigate in real-time in order to apply the anesthetic to the correct target nerve. Thus, the system and method of the present disclosure provides an improved method for detecting, identifying, and mapping the target anatomical object of interest 30 in the various scenes 12 captured in images 14 so that the anesthetic can be delivered quickly and accurately to block the nerve associated with the target anatomical object of interest 30, whereby directions are provided to the user to navigate around the surrounding additional anatomical objects 32, landmarks, tissue, etc.

Figure 11:
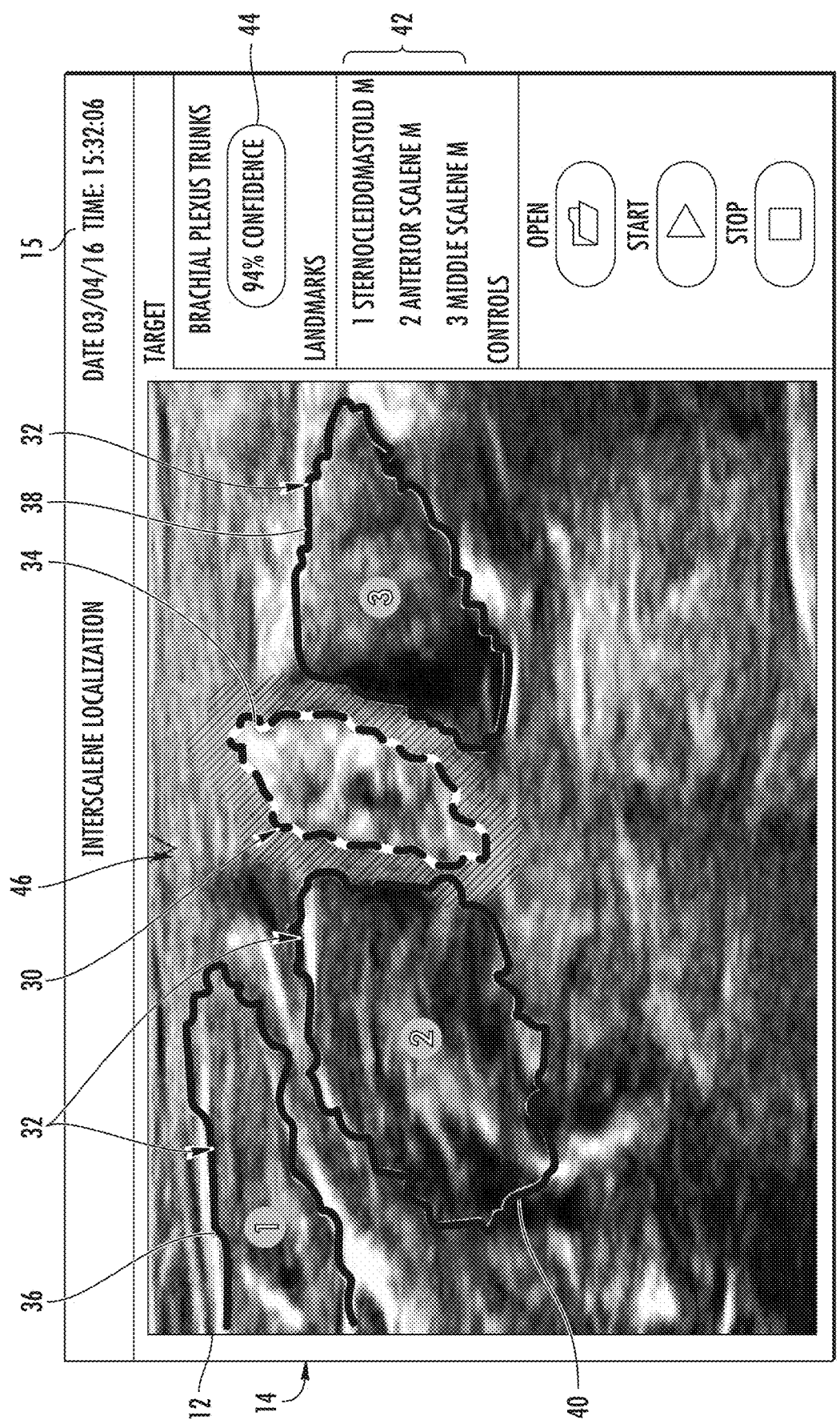
FIG. 11 illustrates a schematic diagram of a real-time ultrasound image of a scene of an anatomical region around an interscalene nerve block generated by an imaging system according to the present disclosure, where the anatomical objects and surrounding tissue of interest have been detected and identified with outlining and numbering.
Figure 12:
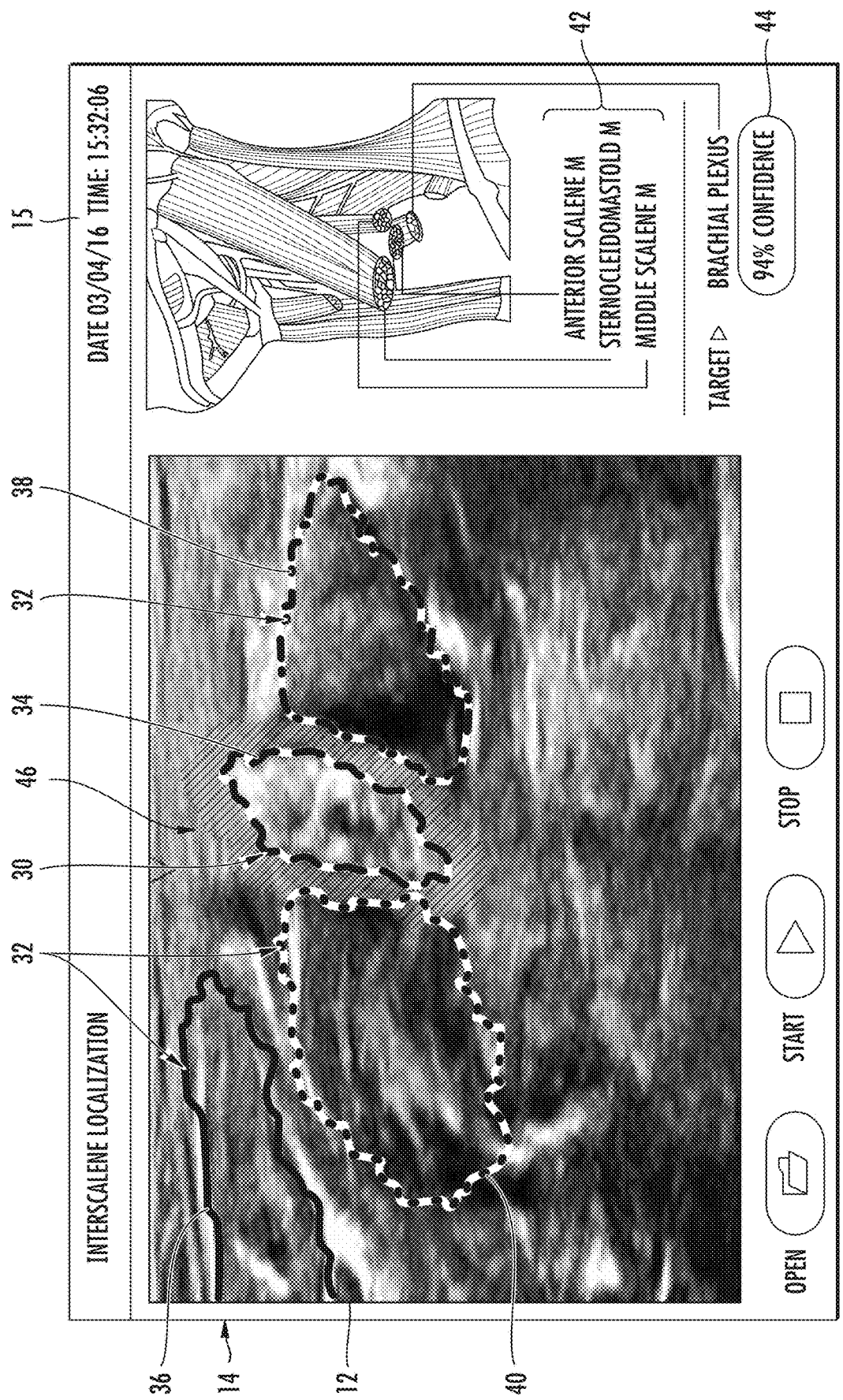
FIG. 12 illustrates a schematic diagram of another embodiment of a real-time ultrasound image of a scene of an anatomical region around an interscalene nerve block generated by an imaging system according to the present disclosure, where the anatomical objects and surrounding tissue of interest have been detected and identified with outlining.

It should be understood, however, that the system and method of the present disclosure may be used for any variety of medical procedures involving any anatomy structure in addition to those relating to the brachial plexus 34. For example, the target anatomical object(s) of interest 30 and the surrounding additional anatomical objects 32 or tissue may be from any anatomical region discussed above with respect to the nerve blocks described in FIG. 1 or from any other anatomical region around which a medical procedure is to be performed. Further, as shown in FIGS. 11 and 12, the image 14 generated by the imaging system 10 may include the scene 12 from the anatomical region surrounding the target anatomical object of interest 30 as well as an optional task bar 15 located adjacent thereto. In addition, the task bar 15 may include other suitable control features such as open, start, and stop buttons as well as the date and time. In alternative embodiments, the task bar 15 may be omitted. It should also be understood that the image 14 may further include any other suitable control and/or display features and may be controlled via the user interface 22 or via touch-screen capabilities.

Figure 7:
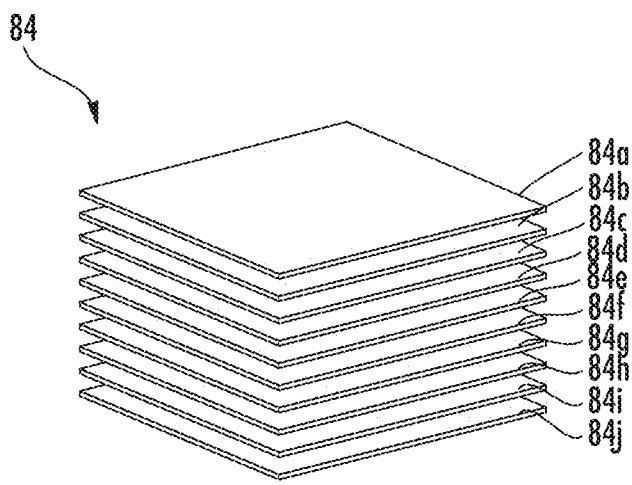
FIG. 7 illustrates a dataset containing a plurality of two-dimensional sliced images, where the dataset is used to train a deep learning network, where the deep learning network is used to detect, identify, label, and map the anatomical object of interest, additional anatomical objects, and landmarks contained in the real-time ultrasound images of FIG. 6.
Figure 8:
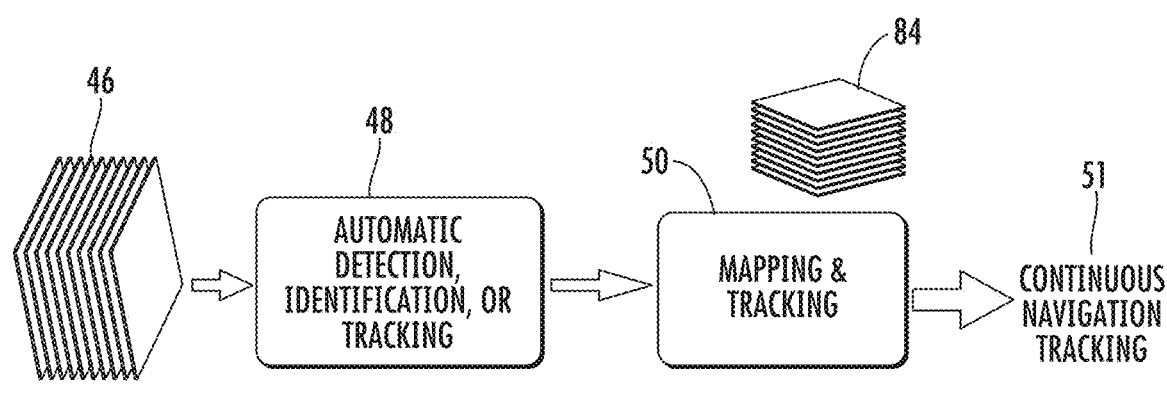
FIG. 8 illustrates a schematic diagram of a method for automatic detection and mapping of scenes from an anatomical region surrounding a target anatomical object of interest in order to provide directions to a user to locate the target anatomical object of interest during a medical procedure.

Referring particularly to FIGS. 6-9, the method of the present invention involves generating a plurality of real-time two-dimensional sliced images 46a, 46b, 46c, 46d, 46e, 46f, 46g, 46h, 46i, and 46j that are collected from an anatomical region surrounding an anatomical object (e.g., target nerve) of interest 30 using the system of the present disclosure. Further, as shown in FIG. 7, a dataset 84 containing a plurality of two-dimensional sliced images 84a, 84b, 84c, 84d, 84e, 84f, 84g, 84h, 84i, and 84j can be previously obtained, where the dataset 84 is used to train a deep learning network, where the deep learning network is used to detect and identify/label scenes from the anatomical region surrounding the target anatomical object, and then map each of the plurality of real-time two-dimensional images from the anatomical region surrounding the target anatomical object based on a relative spatial location and a relative temporal location of each of the identified scenes in the anatomical region contained in the real-time two-dimensional ultrasound images 46a-j of FIG. 6. Then, referring now to FIG. 8, the target anatomical object 30 or 149 and additional anatomical objects 32 and other landmarks/tissue (not shown) contained within scenes of the real-time two-dimensional ultrasound images 46 can be automatically detected, identified, and tracked at block 48, followed by mapping and continued tracking at block 50, utilizing a deep learning network that has been trained to by the dataset of images 84 in order to provide continuous navigational tracking during any medical procedure being performed by a medical professional. It should be understood that although ten real-time two-dimensional images 46a-46j are generated in FIG. 6 and ten images 84a-84j are used to form the training dataset of FIG. 7, it should be understood that depending on the size and complexity of the anatomical region of interest surrounding a particular target anatomical object on which a medical procedure is being performed, any number of real-time two-dimensional images 46 and/or images in the dataset 84 can be obtained. For instance, up to 100,000, such as between about 5 and 50,000, such as between about 10 and about 10,000, or any other suitable number of images of different scenes can be utilized. After the real-time two-dimensional images 46 have been mapped based on the relative spatial and temporal locations of each of the identified scenes in the anatomical region via the deep learning network at block 50, the resulting mapped locations can be used to provide a user with directions/continuous navigation tracking at block 51 to locate the target anatomical object of interest (e.g., target nerve) during a medical procedure (e.g., delivery of a nerve block).

Figure 9:
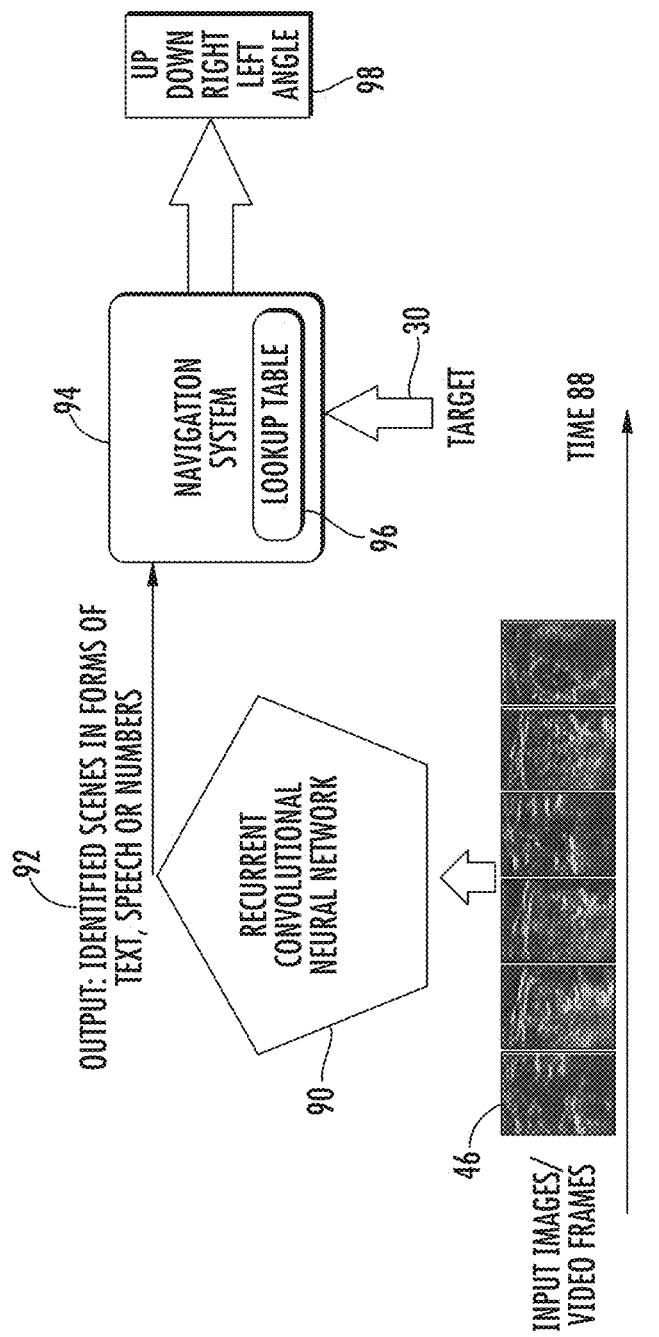
FIG. 9 illustrates a schematic diagram of a method for automatic detection and mapping of scenes from an anatomical region surrounding a target anatomical object of interest in order to provide directions to a user to locate the target anatomical object of interest during medical procedure using a recurrent convolutional neural network.

Referring to FIG. 9, the continuous navigation tracking can be based on the use of a recurrent convolutional neural network 90. The recurrent convolutional neural network 90 can process real-time images 46 over a span of time 88 and can identify the major landmarks present in identified scenes from the images 46, which can be output to the navigation system 94 in the forms of text, speech, numbers, etc. Using a recurrent convolutional neural network 90 can ensure that a history of previously processed frames (such as the data set of images 84) is stored so that the temporal correlation of videos/images can be extracted for more accurate detection and tracking. As shown in FIG. 9, the output 92 of the tracking system can be in the form of text, audio/speech, or assigned labels and numbers. The navigation system 94 then receives the output 92 from the tracking system in order to determine the navigation system knows the current location of probe, instrument, etc. Based on the target anatomical object 149 and the current location of the probe 28 and/or instrument 145, the navigation system 94 can use a pre-programmed lookup table 96 of landmarks to calculate the correct path toward the target anatomical object 149. Then, the navigation system 94 it will provide guidance and directions 98 to the user such as moving the imaging probe 28 and/or instrument 145 to the right, left, up and down as well as changing angles. Such directions 98 can be provided in the form of text or arrows superimposed on the user display or can be in the form of audio/speech.

Figure 10:
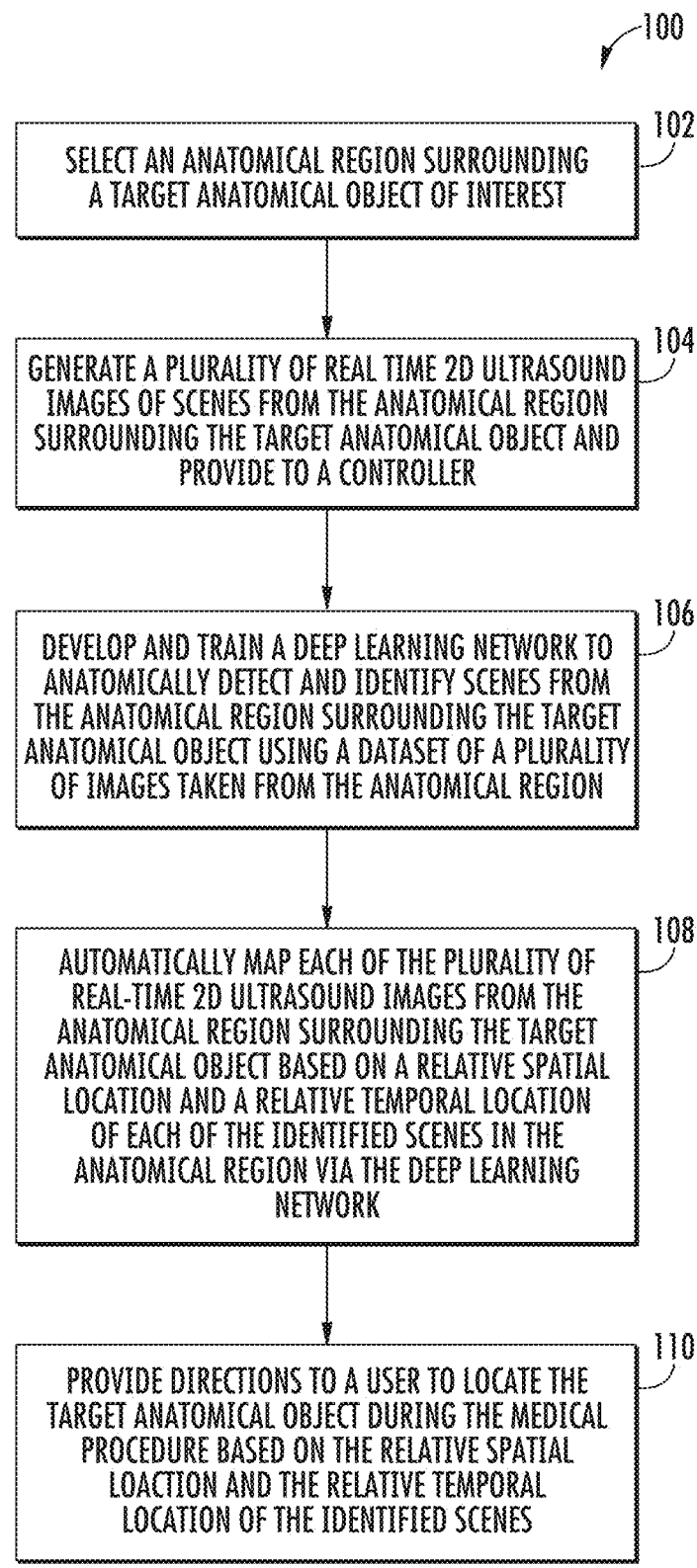
FIG. 10 illustrates a flow diagram of one embodiment of a method for automatic detection and mapping of scenes from an anatomical region surrounding a target anatomical object of interest in order to provide directions to a user to locate the target anatomical object of interest during a medical procedure.

Next, referring particularly to FIG. 10, as shown at 102, the method 100 generally includes selecting an anatomical region surrounding a target anatomical object (e.g., target nerve) of interest. Then, as shown at 104, the method 100 includes generating a plurality of real-time two-dimensional images 46 of scenes 12 from the anatomical region of surrounding the target anatomical object of interest and providing the plurality of real-time two-dimensional images 12 to the controller 17.

As shown at 106, the method 100 also includes developing and training a deep learning network to automatically detect and identify scenes 12 from the anatomical region surrounding the target anatomical object (e.g., additional anatomical objects, landmarks, surrounding tissue, etc.) contained in the real-time two-dimensional ultrasound images 46 using a dataset of two-dimensional images 84 received from a plurality of patients, where the dataset of images 84 is generated by scanning and collecting, for each of the plurality of patients, scenes from a plurality of images from the anatomical region surrounding the target anatomical object of interest. As such, the target anatomical object, additional anatomical objects, landmarks, surrounding tissue, or a combination thereof from each scene 12 contained in the plurality of real-time two-dimensional images 46 for each patient can be labeled or annotated to form a plurality of images 14. More specifically, in certain embodiments, the deep learning network may include one or more deep convolutional neural networks (CNNs), one or more recurrent neural networks, or any other suitable neural network configurations. In machine learning, deep convolutional neural networks generally refer to a type of feed-forward artificial neural network in which the connectivity pattern between its neurons is inspired by the organization of the animal visual cortex, whose individual neurons are arranged in such a way that they respond to overlapping regions tiling the visual field. In contrast, recurrent neural networks (RNNs) generally refer to a class of artificial neural networks where connections between units form a directed cycle. Such connections create an internal state of the network which allows the network to exhibit dynamic temporal behavior. Unlike feed-forward neural networks (such as convolutional neural networks), RNNs can use their internal memory to process arbitrary sequences of inputs. As such, RNNs can extract the correlation between the image frames in order to better identify and track anatomical objects in real time.

In certain embodiments, the controller 17 may use ground truth data to train and/or develop the deep neural network to automatically detect and identify the scenes 12 of the real-time two-dimensional images 46 containing the target anatomical object 30 or 149, landmarks 42, and/or additional anatomical objects (e.g., tissue) 32. For example, in particular embodiments, the controller 17 may be configured to initially train the deep neural network to automatically detect and identify the scenes 12 containing the target anatomical object(s) 30 or 149, additional anatomical objects 32, landmarks 42, etc. More specifically, in certain embodiments, the initial training may be completed while the controller 17 is offline. In another embodiment, the controller 17 may be configured to continuously train the deep neural network online to automatically detect the scenes 12 containing the target anatomical object(s) 30 or 149, additional anatomical objects 32, landmarks 42, etc. after the initial training is complete.

More specifically, in particular embodiments, the controller 17 may be configured for online learning to continuously train the deep neural network from newly captured data in the field to automatically detect the target anatomical object 30 or 149, additional anatomical objects 32, landmarks 42, etc. present in the scene 12 by scanning and collecting a dataset of images 84 of the target anatomical object 30 or 149, additional anatomical objects 32, landmarks 42, etc. from multiple patients. For example, in certain embodiments, hundreds and/or thousands of images may be scanned and collected from multiple patients and stored in the dataset of images 84 via the memory device(s) 18. Further, before storing, the dataset of images 84 may be annotated based on user input to create the ground truth data. For example, in certain embodiments, physicians may annotate and manually identify the dataset of images 84 based on expert knowledge to assist the deep learning network in detecting and identifying the target anatomical object(s) 30, additional anatomical objects 32, landmarks 42, etc. in each image of the dataset. As such, the ground truth data as described herein generally refers to information provided by direct observation of experts in the field as opposed to information provided by inference. Thus, the deep learning network of the present disclosure is configured to mimic a human brain during operation.

In particular embodiments, the dataset of images 84 can then be divided into a plurality of groups. For example, in one embodiment, the ground truth data may be divided into at least two groups including a training dataset and a validation dataset. As such, in particular embodiments, the controller 17 is configured to utilize the training dataset to train the parameter space deep neural network. More specifically, in certain embodiments, the controller 17 may be configured to optimize a cost function to minimize an error between an output of the deep neural network and the ground truth data. For example, in one embodiment, the step of optimizing the cost function to minimize the error may include utilizing a stochastic approximation, such as a stochastic gradient descent (SGD) algorithm, that iteratively processes portions of the ground truth data and adjusts one or more parameters of the deep neural network based on the error between the output of the deep neural network and the ground truth data. As used herein, a stochastic gradient descent generally refers to a stochastic approximation of the gradient descent optimization method for minimizing an objective function that is written as a sum of differentiable functions. More specifically, in one embodiment, the controller 17 may be configured to implement supervised learning to minimize the error between the output of the deep neural network and the ground truth data. As used herein, "supervised learning" generally refers to the machine learning task of inferring a function from labeled training data.

However, it should be understood that the cost function can be defined in different ways such as mean squared error, dice coefficient, categorical cross entropy, etc., and can be optimized using various methods including SGD and its variants such as Adam, Adadelta, Nestrov, etc. In additional embodiments, the processor(s) 16 may implement further deep learning techniques, such as reinforcement learning to train a computer agent to detect anatomical objects in medical images, unsupervised learning to pre-train neural networks and cluster objects using unlabeled data, and/or any other techniques now known or later developed in the art. Such methods may require less training data and/or rely on a reward/punishment function such that the systems do not need to be specifically provided with labeled data.

In another embodiment, the method 100 may also include, after optimizing the cost function, utilizing the deep learning network in real-time to automatically provide predictions on the validation data as well the newly captured data. Thus, in such embodiments, the controller 17 may be configured to compare the predictions with the ground truth data to ensure that the deep neural network is able to generalize. In other words, the controller 17 may be configured to ensure that the deep neural network can provide accurate predictions for cases falling outside of the training data.

Referring still to FIG. 10, as shown at 108, the method 100 also includes automatically mapping each of the plurality of real-time two-dimensional ultrasound images 46 from the anatomical region surrounding the target anatomical object of interest based on the relative spatial location and the relative temporal of each of the identified scenes in the anatomical region. The mapping can be based on the identified scenes from the tracking system and a lookup table that is programmed into the system, as discussed above with respect to FIG. 9.

Referring still to FIG. 10, as shown at 110, the method further includes providing directions to a user (e.g., medical professional) to locate the target anatomical object of interest (e.g., target nerve) during a medical procedure (e.g., delivery of a nerve block via, for instance, the needle 45 shown in FIG. 5), based on the relative spatial location and the relative temporal location of each of the scenes identified in the plurality of real-time two dimensional images 46. The directions can be provided to the user in annotated form on the user display 20 of the imaging system 10 as the user moves an instrument 145 (e.g., needle 45 in FIG. 2) towards the target anatomical object 149 (e.g., target nerve 49 in FIG. 2), where the probe 28 simultaneously scans the anatomical region of interest and the imaging system 10 simultaneously generates the plurality of real-time two-dimensional images 46. It is also to be understood that the directions can be provided in the form of audio instructions, either alone or in combination with the annotated directions present on the user display 20 of the imaging system 10. As the medical professional/user scans an area near the target anatomical object 30 or 149, its current location can be identified using the recurrent convolutional neural network (tracking system) described in FIG. 9, and the path to reach the target anatomical object 30 or 149 (see, i.e., FIG. 5) can be calculated by the navigation system 94 of FIG. 9. Based on the path, directions will be given in the form of arrows, text, or audio/speech to instruct the medical professional/user to move the probe 28 and/or instrument 145 to the right, left, top, bottom, etc. of the current location as well as changing the probe angle or instrument angle with respect to the surface (patient's skin 81) so that the target anatomical object 30 or 149 can be accurately located for imaging or performance of a medical procedure (e.g., nerve block).

Turning now to FIGS. 11-14, when the medical procedure is a nerve block and the imaging system is an ultrasound imaging system, various images 14 obtained from the real-time ultrasound images 46 are shown, where the controller 17 has been configured to label the anatomical object(s) 30, landmarks 42, and/or surrounding tissue 32 on the image 14. More specifically, in certain embodiments, the controller 17 may be configured to outline the target anatomical object 30, additional anatomical objects 32, etc. on the image 14. For example, as shown in FIGS. 11 and 12, the brachial plexus 34 (i.e., the target anatomical object 30) is outlined with a border having a first thickness or pattern. In addition, as shown, various surrounding additional anatomical objects/tissues 32 can be outlined with a border having a second thickness that different from than the first thickness or pattern that is used to outline the brachial plexus 34. As such, a user can easily identify and distinguish the target anatomical object(s) 30 of interest from the additional anatomical objects/tissue 32 in the anatomical region.

Figure 13:
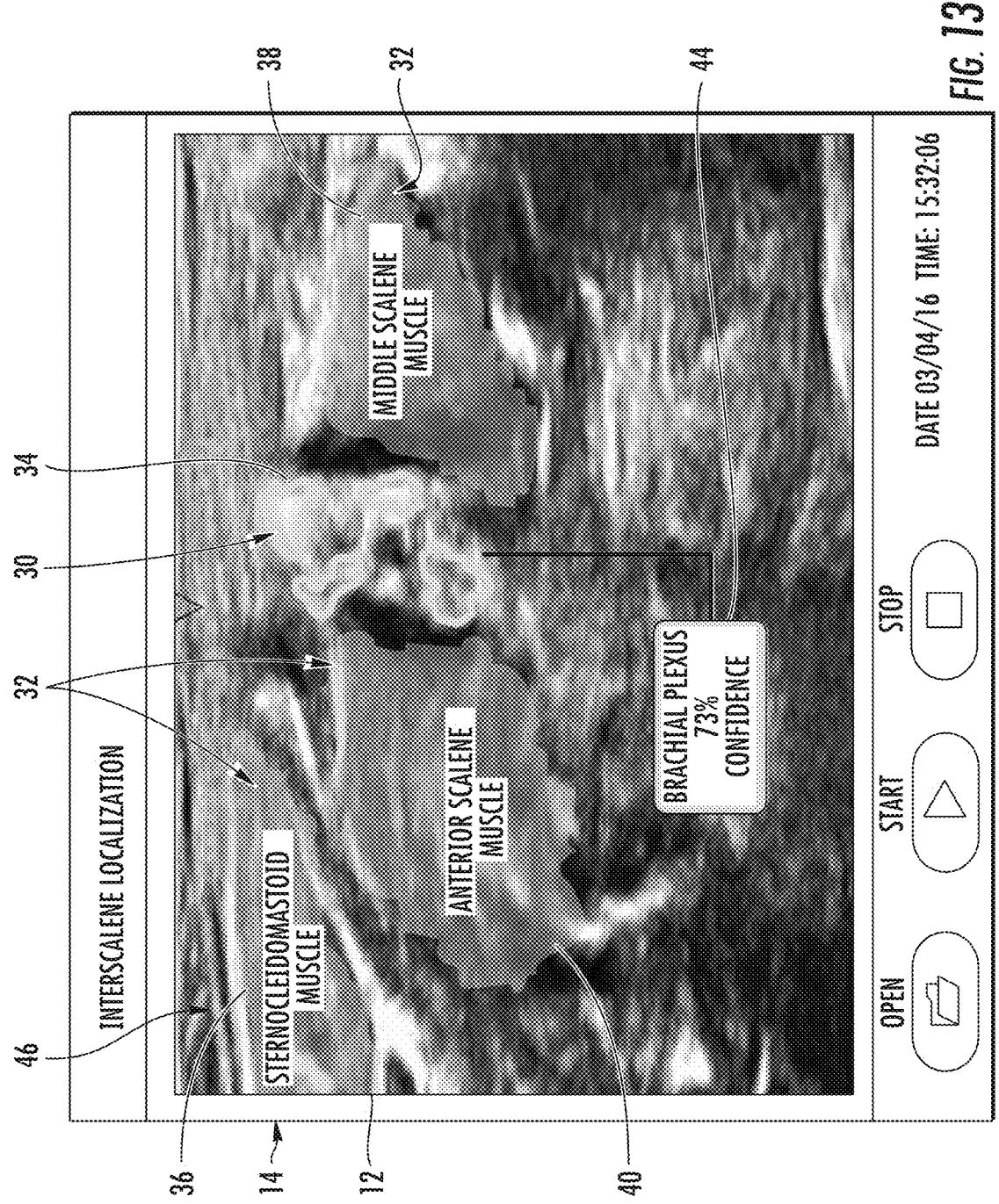
FIG. 13 illustrates a schematic diagram of yet another embodiment of a real-time ultrasound image of a scene of an anatomical region around an interscalene nerve block generated by an imaging system according to the present disclosure, where the anatomical objects and surrounding tissue of interest have been detected and identified with shading, outlining, and labeling.

In further embodiments, the controller 17 can be configured to overlay a descriptive label atop the target anatomical object(s) 30 and/or surrounding additional anatomical objects/tissue 32 on the real-time two-dimensional ultrasound image 46 to obtain various annotated images 14. For example, as shown in FIG. 11, the surrounding anatomical objects/tissue 32 may be numbered and labeled as landmarks 42 (e.g. on the right side of the image 14) for easy identification via a physician. Alternatively, as shown in FIG. 12, the surrounding anatomical objects/tissue 32 may be identified and distinguished by line type and identified as landmarks 42 particularly illustrating a location within the body of the patient. In still another embodiment, as shown in FIG. 13, the surrounding anatomical objects/tissue 32 may be shaded and labeled using a descriptive medical name. In further embodiments, as shown in FIG. 13, the target anatomical object(s) 30 may also be further defined and/or segmented. As such, in the case of the brachial plexus 34, a user can easily identify separate nerves or nerve bundles during a nerve block procedure.

Figure 14:
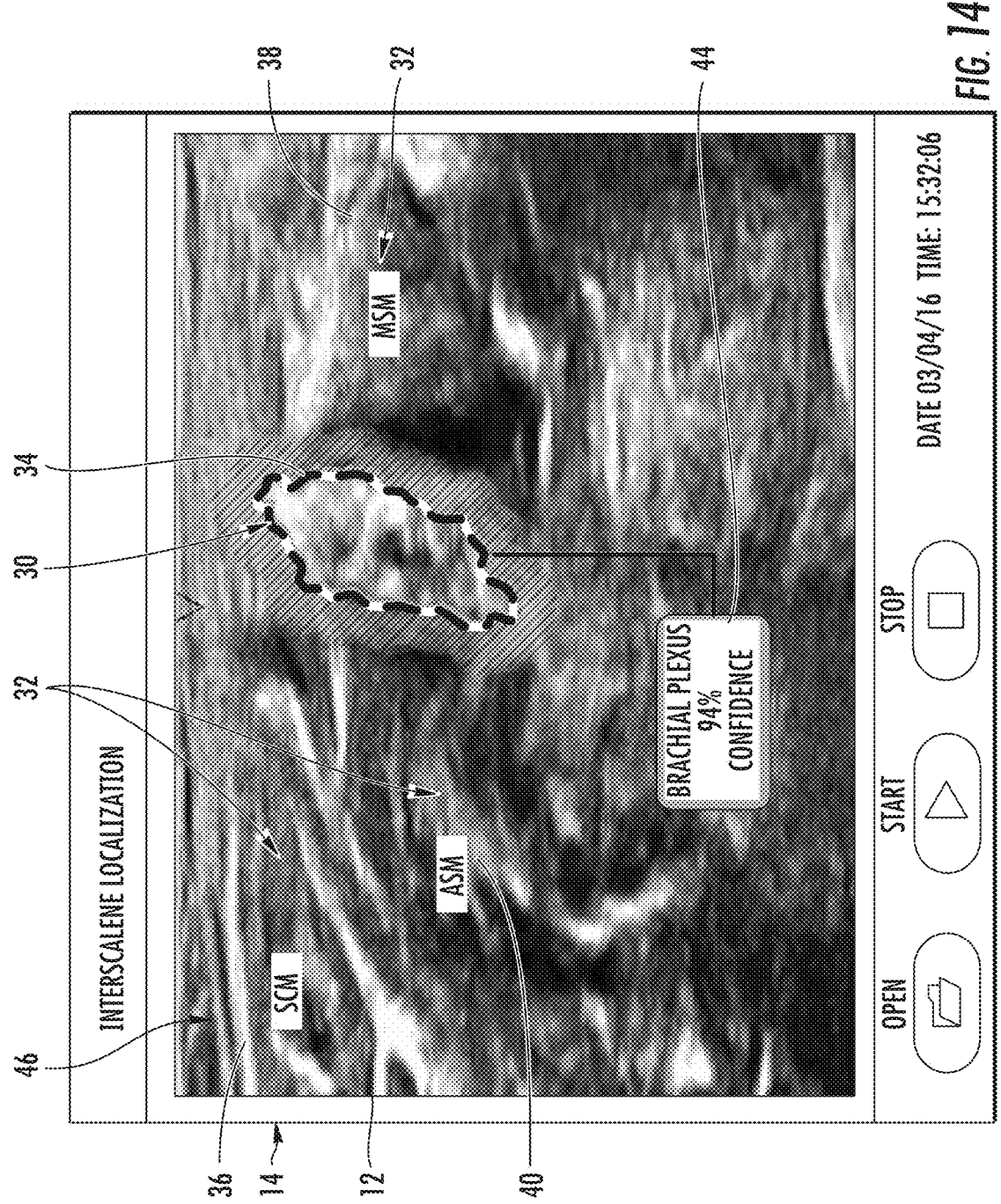
FIG. 14 illustrates a schematic diagram of one more embodiment of a real-time ultrasound image of a scene of an anatomical region around an interscalene nerve block generated by an imaging system according to the present disclosure, where the anatomical objects and surrounding tissue of interest have been detected and identified with shading, outlining, and labeling.

In additional embodiments, as shown in FIGS. 11-14, the controller 17 may also be configured to determine a confidence level 44 of the target anatomical object 30 and/or the surrounding anatomical objects/tissue 32. For example, as shown in FIGS. 11 and 12, the confidence level 44 of the location of the brachial plexus 34 is located on the task bar 15 of the image 14. Alternatively, as shown in FIGS. 13 and 14, the confidence level 44 of the location of the brachial plexus 34 may be located within the identified scene 12 of the image 14, e.g. adjacent to the target anatomical object 30.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for providing navigational directions to a user to locate a target anatomical object during a medical procedure via a medical imaging system, wherein the method is computer-implemented, the method comprising:

selecting an anatomical region surrounding the target anatomical object;

generating a plurality of real-time two-dimensional images of scenes from the anatomical region surrounding the target anatomical object and providing the plurality of real-time two-dimensional images to a controller;

developing and training a deep learning network to automatically detect and identify the scenes from the anatomical region surrounding the target anatomical object via ground truth data by scanning and collecting a dataset of a plurality of images of scenes from the anatomical region surrounding the target anatomical object from each of a plurality of patients; annotating the dataset of images based on user input to create the ground truth data; dividing the dataset of images and the ground truth data into a training dataset and a validation dataset; and utilizing the training dataset to train the deep learning network, wherein the deep learning network comprises a feed-forward neural network, a recurrent neural network, or a combination thereof;

automatically mapping each of the plurality of real-time two-dimensional images from the anatomical region surrounding the target anatomical object based on a relative spatial location and a relative temporal location of each of the identified scenes in the anatomical region via the deep learning network; and providing directions to the user to locate the target anatomical object during the medical procedure based on the relative spatial location and the relative temporal location of each of the identified scenes.

2. The method of claim 1, wherein the medical procedure is a nerve block, wherein the target anatomical object is a target nerve.

3. The method of claim 2, wherein the nerve block comprises an interscalene nerve block, a supraclavicular nerve block, an infraclavicular nerve block, an axillary nerve block, a femoral nerve block, a sciatic nerve block, an adductor canal nerve block, a popliteal nerve block, a saphenous nerve block, a fascia iliaca nerve block, a thoraco lumbar paravertebral nerve block, a transversus abdominus plane (TAP) nerve block, an intercostal nerve block, or a thoracic paravertebral nerve block.

4. The method of claim 1, wherein the deep learning network comprises a convolutional neural network.

5. The method of claim 1, wherein utilizing the training dataset to train the deep learning network further comprises optimizing a cost function to minimize an error between an output of the deep learning network and the ground truth data.

6. The method of claim 5, wherein optimizing the cost function to minimize the error further comprises utilizing a stochastic gradient descent (SOD) algorithm that iteratively processes portions of the ground truth data and adjusts one or more parameters of the deep learning network based on the error between the output of the deep learning network and the ground truth data.

7. The method of claim 6, further comprising, after optimizing the cost function, utilizing the deep learning network in real-time to automatically provide predictions on the validation data and comparing the predictions with the ground truth data.

8. The method of claim 1, wherein annotating the dataset of images based on user input to create the ground truth data further comprises manually identifying and annotating the target anatomical object, additional anatomical objects, landmarks, tissue, or a combination thereof in each image of the dataset.

9. The method of claim 1, further comprising initially training the deep learning network to automatically detect and identify the scenes from the anatomical region surrounding the target anatomical object offline.

10. The method of claim 1, further comprising continuously training the deep learning network to automatically detect and identify the scenes from the anatomical region surrounding the target anatomical object online.

11. The method of claim 1, wherein the directions are provided to the user in annotated form via a user display of the imaging system as a probe scans the anatomical region of interest, wherein the imaging system simultaneously generates the plurality of real-time two-dimensional images.

12. The method of claim 1, wherein directions are provided to the user in audio form as a probe scans the anatomical region of interest, wherein the imaging system simultaneously generates the plurality of real-time two-dimensional images.

13. The method of claim 1, wherein the medical imaging system comprises an ultrasound imaging system, a computed tomography (CT) imaging system, a magnetic resonance (MR) imaging system, or a fluoroscopic imaging system.

14. A medical imaging system for use in a medical procedure, the medical imaging system comprising:
at least one controller configured to perform operations comprising:
receiving a plurality of real-time two-dimensional images of scenes from an anatomical region surrounding a target anatomical object;
developing and training a deep learning network to automatically detect and identify the scenes from the anatomical region surrounding the target anatomical object via ground truth data by scanning and collecting a dataset of a plurality of images of scenes from the anatomical region surrounding the target anatomical object from each of a plurality of patients; annotating the dataset of images based on user input to create the ground truth data; dividing the dataset of images and the ground truth data into a training dataset and a validation dataset; and utilizing the training dataset to train the deep learning network, wherein the deep learning network comprises a feed-forward neural network, a recurrent neural network, or a combination thereof;
automatically mapping each of the plurality of real-time two-dimensional images from the anatomical region surrounding the target anatomical object based on a relative spatial location and a relative temporal location of each of the identified scenes in the anatomical region via the deep learning network; and
providing directions to the user to locate the target anatomical object during the medical procedure based on the relative spatial location and the relative temporal location of each of the identified scenes; and
a user display configured to display the plurality of real-time two-dimensional images to a user.

15. The medical imaging system of claim 14, wherein the medical procedure is a nerve block, wherein the target anatomical object is a target nerve.

16. The medical imaging system of claim 14, wherein the deep learning network comprises a convolutional neural network.

17. The medical imaging system of claim 14, wherein annotating the dataset of images based on user input to create the ground truth data further comprises manually identifying and annotating the target anatomical object, additional anatomical objects, landmarks, tissue, or a combination thereof in each image of the dataset.

18. The medical imaging system of claim 14, wherein the controller is configured to initially train the deep learning network to automatically detect and identify scenes from the anatomical region surrounding the target anatomical object offline.

19. The medical imaging system of claim 14, wherein the controller is configured to continuously train the deep learning network to automatically detect and identify scenes from the anatomical region surrounding the target anatomical object online.

20. The medical imaging system of claim 14, wherein the controller provides directions to the user in annotated form via the user display as a probe scans the anatomical region of interest, wherein the imaging system simultaneously generates the plurality of real-time two-dimensional images.

21. The medical imaging system of claim 14, wherein the controller provides directions to the user in audio form as a probe scans the anatomical region of interest, wherein the imaging system simultaneously generates the plurality of real-time two-dimensional images.

22. The medical imaging system of claim 14, wherein the medical imaging system comprises an ultrasound imaging system, a computed tomography (CT) imaging system, a magnetic resonance (MR) imaging system, or a fluoroscopic imaging system.

23. The medical imaging system of claim 14, wherein the medical imaging system is configured as a software package to be installed and hosted by other medical imaging systems, wherein the medical imaging system can receive images from a host medical imaging system and provide outputs to be deployed by the host medical imaging system.

24. The medical imaging system of claim 14, wherein the deep learning network employs quantized weights, binary weights, and other compression methods to reduce memory usage and accelerate the execution time, such as when limited computation power is available.

25. The medical imaging system of claim 14, wherein the medical imaging system employs transformation, equalization, and normalization techniques to be able to work with different medical imaging systems having different settings, specifications, and image quality.

* * * * *